United States Patent
Yang et al.

(10) Patent No.: US 10,399,068 B2
(45) Date of Patent: *Sep. 3, 2019

(54) SCM-10 MOLECULAR SIEVE, PROCESS FOR PRODUCING SAME AND USE THEREOF

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Weimin Yang, Shanghai (CN); Zhendong Wang, Shanghai (CN); Hongmin Sun, Shanghai (CN); Bin Zhang, Shanghai (CN); Yi Luo, Shanghai (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/347,094

(22) Filed: Nov. 9, 2016

(65) Prior Publication Data
US 2017/0128923 A1    May 11, 2017

(30) Foreign Application Priority Data
Nov. 9, 2015 (CN) .......................... 2015 1 0755226

(51) Int. Cl.
| | |
|---|---|
| *C01B 39/48* | (2006.01) |
| *B01J 29/70* | (2006.01) |
| *B01J 29/86* | (2006.01) |
| *C01B 39/06* | (2006.01) |
| *B01J 29/88* | (2006.01) |
| *B01J 20/18* | (2006.01) |
| *B01J 29/87* | (2006.01) |
| *C01B 39/12* | (2006.01) |
| *B01J 29/04* | (2006.01) |
| *B01J 29/89* | (2006.01) |
| *C07C 2/66* | (2006.01) |

(52) U.S. Cl.
CPC .............. *B01J 29/86* (2013.01); *B01J 20/18* (2013.01); *B01J 29/047* (2013.01); *B01J 29/70* (2013.01); *B01J 29/87* (2013.01); *B01J 29/88* (2013.01); *B01J 29/89* (2013.01); *C01B 39/06* (2013.01); *C01B 39/12* (2013.01); *C01B 39/48* (2013.01); *C07C 2/66* (2013.01); *C01P 2002/72* (2013.01); *C07C 2529/04* (2013.01); *C07C 2529/86* (2013.01)

(58) Field of Classification Search
CPC ......... C01B 39/12; C01B 39/48; C01B 39/06; B01J 29/04; B01J 29/86; B01J 29/89; B01J 29/047; B01J 29/70; B01J 29/87; B01J 29/88; B01J 20/18; C01P 2002/72
See application file for complete search history.

(56) References Cited

U.S. PATENT DOCUMENTS

| | | | |
|---|---|---|---|
| 2,882,243 A | 4/1959 | Milton | |
| 2,882,244 A | 4/1959 | Milton | |
| 3,130,007 A | 4/1964 | Breck | |
| 3,702,886 A | 11/1972 | Argauer et al. | |
| 4,390,457 A | 6/1983 | Klotz | |
| 4,410,501 A | 10/1983 | Taramasso et al. | |
| 6,080,382 A * | 6/2000 | Lee ..................... | B01D 53/8628 208/111.01 |
| 6,706,938 B2 * | 3/2004 | Roeseler ................... | C07C 7/13 585/820 |
| 8,372,377 B2 * | 2/2013 | Lorgouilloux ........... | B01J 20/18 210/660 |
| 2011/0011810 A1 | 1/2011 | Lorgouilloux et al. | |
| 2011/0130579 A1 | 6/2011 | Müller et al. | |

(Continued)

FOREIGN PATENT DOCUMENTS

| | | |
|---|---|---|
| JP | 4990145 B2 | 8/2012 |
| TW | 201524599 A | 7/2015 |

OTHER PUBLICATIONS

Jose G. Nery et al. On the synthesis of SSZ-48, SSZ-43 and their variations, Microporous and Mesoporous Materials, Jan. 3, 2002, pp. 19-28, vol. 52, Issue 1, Elsevier.

(Continued)

*Primary Examiner* — David M Brunsman
(74) *Attorney, Agent, or Firm* — Novick, Kim & Lee, PLLC; Allen Xue

(57) ABSTRACT

The present invention relates to an SCM-10 molecular sieve, a process for producing same and use thereof. The molecular sieve has an empirical chemical composition as illustrated by the formula "the first oxide·the second oxide", wherein the ratio by molar of the first oxide to the second oxide is less than 40, the first oxide is at least one selected from the group consisting of silica and germanium dioxide, the second oxide is at least one selected from the group consisting of alumina, boron oxide, iron oxide, gallium oxide, titanium oxide, rare earth oxides, indium oxide and vanadium oxide. The molecular sieve has specific XRD pattern and can be used as an adsorbent or a catalyst for converting an organic compound.

21 Claims, 1 Drawing Sheet

(56) References Cited

U.S. PATENT DOCUMENTS

2017/0128918 A1* 5/2017 Yang ..................... B01J 29/047
2017/0128923 A1* 5/2017 Yang ..................... B01J 29/86
2017/0128924 A1* 5/2017 Yang ..................... B01J 29/86

OTHER PUBLICATIONS

Paul Wagner et al. Electron diffraction structure solution of a Nanocrystalline Zeolite at Atomic Resolution, J. Phys. Chem. B, Sep. 11, 1999, pp. 8245-8250, 103 (39), 10.121/jp991389j, 1999 American Chemical Society.

* cited by examiner

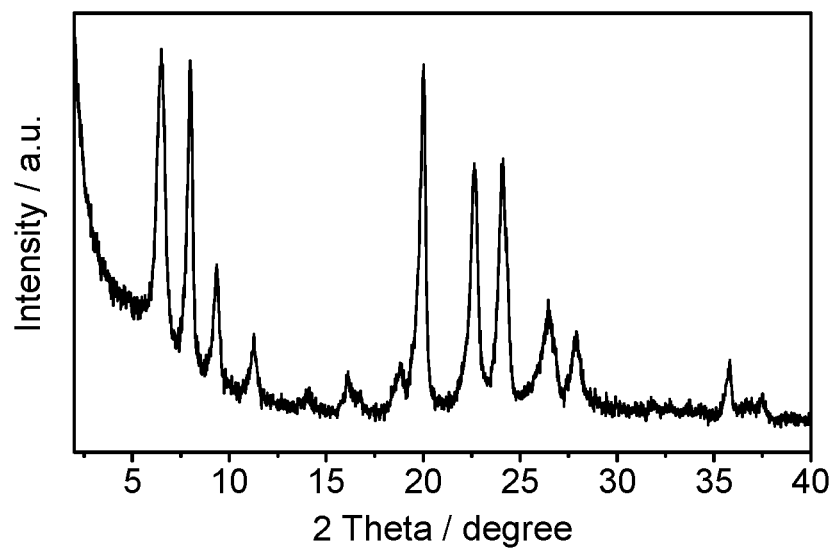

SCM-10 MOLECULAR SIEVE, PROCESS FOR PRODUCING SAME AND USE THEREOF

TECHNICAL FIELD

The present invention relates to an SCM-10 molecular sieve, a process for producing same and use thereof.

BACKGROUND ART

In industry, porous inorganic materials have been widely used as catalysts and catalyst carriers. These porous materials generally include amorphous porous materials, crystalline molecular sieves and modified layered materials. Minute difference in the structure between any two materials may indicate significant difference in properties like catalytic performance and adsorbing ability therebetween, and further difference in available parameters used to characterize same, such as morphology, specific surface area or pore size.

The structure of a molecular sieve is specifically confirmed by the X-ray diffraction pattern (XRD), while the X-ray diffraction pattern (XRD) is determined by X-ray powder diffraction with a Cu—K α-ray source and a Ni filter. Different molecular sieves have different characterizing XRD patterns. Known molecular sieves, like A-Type Zeolite, Y-Type Zeolite, MCM-22 molecular sieve and so on, have their characterizing XRD patterns respectively.

At the same time, two molecular sieves, if sharing the same characterizing XRD pattern but comprising different combination of skeleton elements, will be identified as different molecular sieves. For example, TS-1 molecular sieve (U.S. Pat. No. 4,410,501) and ZSM-5 molecular sieve (U.S. Pat. No. 3,702,886), share the same characterizing XRD pattern but comprise different combination of skeleton elements. Specifically, TS-1 molecular sieve comprises Si and Ti as the skeleton elements, exhibiting a catalytic oxidation ability, while ZSM-5 molecular sieve comprises Si and Al as the skeleton elements, exhibiting an acidic catalytic ability.

Further, two molecular sieves, if sharing the same characterizing XRD pattern and the same combination of skeleton elements but with different relative amounts of the skeleton elements, will be identified as different molecular sieves as well. For example, Zeolite X (U.S. Pat. No. 2,882,244) and Zeolite Y (U.S. Pat. No. 3,130,007), share the same characterizing XRD pattern and the same combination of skeleton elements (Si and Al), but with different relative amounts of Si and Al. Specifically, Zeolite X has a Si/Al molar ratio of less than 1.5, while Zeolite Y has a Si/Al molar ratio of greater than 1.5.

INVENTION SUMMARY

The present inventors, on the basis of the prior art, found a novel molecular sieve having the SFE structure, and further identified beneficial properties for same.

Specifically, this invention relates to the following aspects.

1. An SCM-10 molecular sieve, having an empirical chemical composition as illustrated by the formula "the first oxide·the second oxide", wherein the ratio by molar of the first oxide to the second oxide is less than 40, preferably in the range of from 3 to less than 40, more preferably 5-30, the first oxide is at least one selected from the group consisting of silica and germanium dioxide, preferably silica, the second oxide is at least one selected from the group consisting of alumina, boron oxide, iron oxide, gallium oxide, titanium oxide, rare earth oxides, indium oxide and vanadium oxide, preferably boron oxide or a combination of boron oxide and at least one selected from the group consisting of alumina, iron oxide, gallium oxide, titanium oxide, rare earth oxides, indium oxide and vanadium oxide, more preferably boron oxide or a combination of boron oxide and alumina, more preferably boron oxide, and the molecular sieve in the calcined form has X ray diffraction pattern as substantially illustrated in the following table,

| 2θ (°) [a] | d-spacing (Å) [b] | Relative intensity ($I/I_0 \times 100$) |
|---|---|---|
| 6.50 | 13.59 | w-s |
| 7.98 | 11.07 | s-vs |
| 9.36 | 9.45 | m |
| 11.27 | 7.85 | w-m |
| 20.02 | 4.43 | s |
| 22.65 | 3.92 | vs |
| 24.13 | 3.69 | vs |
| 26.45 | 3.37 | w-m |
| 27.92 | 3.19 | w-m |
| 35.95 | 2.50 | m |

[a] ±0.3°,
[b] changed with 2θ.

2. The SCM-10 molecular sieve according to anyone of the preceding aspects, wherein the X-ray diffraction pattern further includes X-ray diffraction peaks as substantially illustrated in the following table,

| 2θ (°) [a] | d-spacing (Å) [b] | Relative intensity ($I/I_0 \times 100$) |
|---|---|---|
| 14.12 | 6.27 | w |
| 16.12 | 5.49 | w |
| 18.82 | 4.71 | w |
| 37.52 | 2.40 | w |

[a] ±0.3°,
[b] changed with 2θ.

3. A process for producing an SCM-10 molecular sieve, including a step of crystallizing a mixture comprising a first oxide source, a second oxide source, an organic template and water to obtain the molecular sieve, and optionally, a step of calcining the obtained molecular sieve, wherein the organic template is selected from a compound represented by the following formula (A), a quaternary ammonium salt thereof and a quaternary ammonium hydroxide thereof, preferably 4-dimethylamino pyridine,

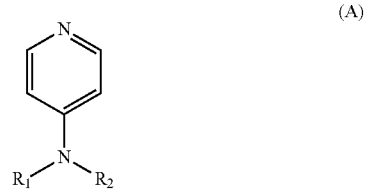

(A)

wherein $R_1$ and $R_2$ may be identical to or different from each other, each independently representing a $C_{1-8}$ alkyl, preferably a $C_{1-4}$ alkyl, more preferably a $C_{1-2}$ alkyl.

4. The process according to anyone of the preceding aspects, wherein the mixture does not contain an alkaline source.

5. The process according to anyone of the preceding aspects, wherein the mixture does not contain a fluorine source.

6. The process according to anyone of the preceding aspects, wherein the mixture has a pH=6-14, preferably pH=7-14, more preferably 8-14, more preferably 8.5-13.5, more preferably 9-12, more preferably 9-11.

7. The process according to anyone of the preceding aspects, wherein the first oxide source is at least one selected from the group consisting of a silicon source and a germanium source, preferably a silicon source, the second oxide source is at least one selected from the group consisting of an aluminum source, a boron source, an iron source, a gallium source, a titanium source, a rare earth source, an indium source and a vanadium source, preferably a boron source or a combination of a boron source and at least one selected from the group consisting of an aluminum source, an iron source, a gallium source, a titanium source, a rare earth source, an indium source and a vanadium source, more preferably a boron source or a combination of a boron source and an aluminum source, more preferably a boron source, the ratio by molar between the first oxide source (as the first oxide), the second oxide source (as the second oxide), the organic template and water is 1:(0.025-1/3):(0.01-1.0):(4-50), preferably 1:(1/30-1/3):(0.02-0.9):(4-40), more preferably 1:(1/30-1/5):(0.04-0.8):(4-30), with the proviso that the ratio by molar of the first oxide source (as the first oxide) to the second oxide source (as the second oxide) is less than 40, preferably less than 30.

8. An SCM-10 molecular sieve composition, comprising the SCM-10 molecular sieve according to anyone of the preceding aspects or an SCM-10 molecular sieve produced in line with the process according to anyone of the preceding aspects, and a binder.

9. Use of the SCM-10 molecular sieve according to anyone of the preceding aspects, an SCM-10 molecular sieve produced in line with the process according to anyone of the preceding aspects or the SCM-10 molecular sieve composition according to anyone of the preceding aspects as an adsorbent or a catalyst for converting an organic compound.

10. Use according to anyone of the preceding aspects, wherein the catalyst for converting an organic compound is at least one selected from the group consisting of an alkane isomerization catalyst, a catalyst for the alkylation between olefins and aromatics, an olefin isomerization catalyst, a naphtha cracking catalyst, a catalyst for the alkylation between alcohols and aromatics, an olefin hydration catalyst and an aromatic disproportionation catalyst.

TECHNICAL EFFECTS

According to the present invention, the SCM-10 molecular sieve has the SFE structure, but with a chemical composition that has never been obtained in this field before.

FIGURE DESCRIPTION

FIG. 1 illustrates the X-ray diffraction pattern (XRD) of the molecular sieve produced in Example 1.

SPECIFIC MODE TO CARRY OUT THIS INVENTION

This invention will be described in details hereinafter with reference to the following specific embodiments. However, it should be noted that the protection scope of this invention should not be construed as limited to these specific embodiments, but rather determined by the attached claims.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention.

Further, to the extent that any meaning or definition of a term in this document conflicts with any meaning or definition of the same term in a document incorporated by reference, the meaning or definition assigned to that term in this document shall govern.

In the context of this specification, a molecular sieve, before any other material (for example, organic templates) than water and metal ions that has been filled into its pores during the production thereof is removed from the pores, is referred to as "precursor".

In the context of this specification, in the XRD data of the molecular sieve, w, m, s, vs indicate the intensity of a diffraction peak, with w referring to weak, m to medium, s to strong, vs to very strong, which has been well known in this field. In general, w represents a value of less than 20; m represents a value of 20-40; s represents a value of 40-70; vs represents a value of greater than 70.

In the context of this specification, the molecular sieve structure is confirmed by the X-ray diffraction pattern (XRD), while the X-ray diffraction pattern (XRD) is determined by X-ray powder diffraction with a Cu—K $\alpha$-ray source and a Ni filter. Before determination, the crystalline state of the test sample is observed under scanning electron microscope (SEM), to confirm that there presents only one type of crystal therein, which indicates that the molecular sieve as the test sample presents as a pure phase, and then the XRD determination is conducted thereon, in order to ensure that there is no interfering peak of other crystal in the XRD pattern. In the context of this specification, by specific surface area, it refers to the total area per unit of mass of a sample, including the internal surface area and the external surface area. A non-porous material has only external surface area, like Portland cement or some clay mineral powder, while a porous material has an external surface area and an internal surface area, like asbestos fiber, diatomite or molecular sieves. In a porous material, the surface area of pores having a diameter of less than 2 nm is referred to as internal surface area, while the surface area obtained by subtracting the internal surface area from the total surface area is referred to as external surface area. The external surface area per unit of mass of a sample is referred to as external specific surface area.

In the context of this specification, by pore volume, it refers to the volume of pores per unit of mass of a porous material (e.g. a molecular sieve). By total pore volume, it refers to the volume of all pores (generally involving only pores having a pore diameter of less than 50 nm) per unit of mass of a molecular sieve. By micropore volume, it refers to the volume of all micropores (generally referred to pores having a pore diameter of less than 2 nm) per unit of mass of a molecular sieve.

The present invention relates to an SCM-10 molecular sieve. The SCM-10 molecular sieve has the SFE structure, but with a chemical composition that has never been obtained in this field before.

According to the present invention, the SCM-10 molecular sieve has an empirical chemical composition as illustrated by the formula "the first oxide·the second oxide". It is known that, a molecular sieve will sometimes (especially immediately after the production thereof) contain a certain amount of water, however, this invention does not specify or identify as to how much this amount may be, since the presence or absence of water will not substantially change the XRD pattern of the present molecular sieve. In this context, the empirical chemical composition actually represents an anhydrous chemical composition of this molecular sieve. Further, it is obvious that the empirical chemical composition represents the framework chemical composition of the molecular sieve.

According to the present invention, in the SCM-10 molecular sieve, the ratio by molar of the first oxide to the second oxide is generally less than 40, preferably in the range of from 3 to less than 40, more preferably 5-30.

According to the present invention, in the SCM-10 molecular sieve, the first oxide is at least one selected from the group consisting of silica and germanium dioxide, preferably silica.

According to the present invention, in the SCM-10 molecular sieve, the second oxide is at least one selected from the group consisting of alumina, boron oxide, iron oxide, gallium oxide, titanium oxide, rare earth oxides, indium oxide and vanadium oxide, preferably boron oxide or a combination of boron oxide and at least one selected from the group consisting of alumina, iron oxide, gallium oxide, titanium oxide, rare earth oxides, indium oxide and vanadium oxide, more preferably boron oxide or a combination of boron oxide and alumina, more preferably boron oxide.

According to one embodiment of the present invention, the first oxide is silica, and the second oxide is boron oxide.

According to another embodiment of the present invention, the first oxide is at least one selected from the group consisting of silica and germanium dioxide, and the second oxide is boron oxide. According to another embodiment of the present invention, the first oxide is silica, and the second oxide is at least one selected from the group consisting of boron oxide and alumina.

According to one embodiment of the present invention, if multiple oxides are used in combination, the ratio by molar between each two oxides is generally 1-99.6:99-0.4, preferably 33-99.5:67-0.5, more preferably 50-99:50-1, more preferably 60-99:40-1, more preferably 66-98:34-2, more preferably 66-97:34-3.

According to the present invention, the molecular sieve in the calcined form has X ray diffraction pattern as substantially illustrated in the following table.

| 2θ (°) [a] | d-spacing (Å) | Relative intensity ($I/I_0 \times 100$) |
|---|---|---|
| 6.50 | 13.62 ± 0.63 | w-s |
| 7.98 | 11.09 ± 0.42 | s-vs |
| 9.36 | 9.45 ± 0.30 | m |
| 11.27 | 7.85 ± 0.21 | w-m |
| 20.02 | 4.43 ± 0.07 | s |
| 22.65 | 3.92 ± 0.05 | vs |
| 24.13 | 3.69 ± 0.05 | vs |
| 26.45 | 3.37 ± 0.04 | w-m |
| 27.92 | 3.19 ± 0.03 | w-m |
| 35.95 | 2.50 ± 0.02 | m |

[a] ±0.3°.

Further, the X-ray diffraction pattern further includes X-ray diffraction peaks as substantially illustrated in the following table,

| 2θ (°) [a] | d-spacing (Å) | Relative intensity ($I/I_0 \times 100$) |
|---|---|---|
| 14.12 | 6.27 ± 0.13 | w |
| 16.12 | 5.50 ± 0.10 | w |
| 18.82 | 4.71 ± 0.07 | w |
| 37.52 | 2.40 ± 0.02 | w |

[a] ±0.3°.

According to the present invention, the SCM-10 molecular sieve has a specific surface area (by the BET method) of 250-600 m²/g, preferably 280-450 m²/g.

According to the present invention, the SCM-10 molecular sieve has a micropore volume (by the t-plot method) of 0.05-0.25 cm³/g, preferably 0.08-0.18 cm³/g.

According to the present invention, the SCM-10 molecular sieve has a pore size (by the Argon adsorption method) of 0.6-0.73 nm, preferably 0.62-0.68 nm.

According to the present invention, the SCM-10 molecular sieve can be produced in line with the following process. In view of this, the present invention further relates to a process for producing an SCM-10 molecular sieve, including a step of crystallizating a mixture comprising a first oxide source, a second oxide source, an organic template and water (hereinafter referred to as the mixture) under crystallization conditions to obtain the molecular sieve (hereinafter referred to as the crystallization step).

According to the present invention, in the process for producing the molecular sieve, the organic template may be a compound represented by the following formula (A), a quaternary ammonium salt thereof or a quaternary ammonium hydroxide thereof, preferably 4-dimethylamino pyridine.

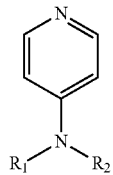

(A)

According to the present invention, in the formula (A), $R_1$ and $R_2$ may be identical to or different from each other, each independently representing a $C_{1-8}$ alkyl, preferably a $C_{1-4}$ alkyl, more preferably a $C_{1-2}$ alkyl, most preferably both methyl.

According to the present invention, as the quaternary ammonium salt of the compound represented by the formula (A), there may be exemplified a quaternary nitrogen ($N^+$) structure obtained by additionally bonding a $C_{1-8}$ alkyl (preferably a $C_{1-4}$ alkyl, more preferably a $C_{1-2}$ alkyl or methyl) to the N atom in addition to the groups $R_1$ and $R_2$. As the counterion of the quaternary nitrogen, there may be exemplified a halo ion like Br⁻, but not limiting thereto.

According to the present invention, as the quaternary ammonium hydroxide of the compound represented by the formula (A), there may be exemplified a quaternary nitrogen ($N^+$) structure obtained by additionally bonding a $C_{1-8}$ alkyl (preferably a $C_{1-4}$ alkyl, more preferably a $C_{1-2}$ alkyl or methyl) to the N atom in addition to the groups $R_1$ and $R_2$. As the counterion of the quaternary nitrogen, a hydroxyl ion (OH⁻) is needed.

According to the present invention, in the process for producing the molecular sieve, the crystallization step may be conducted in any way known in this field, there may be exemplified a way wherein the first oxide source, the second oxide source, the organic template and water are mixed in predetermined ratios, and then the obtained mixture is allowed to hydrothermally crystallize under crystallization conditions.

According to the present invention, in the process for producing the molecular sieve, the crystallization conditions include: a crystallization temperature of 140-210 degrees Celsius, preferably 150-190 degrees Celsius, more preferably 160-180 degrees Celsius, a crystallization duration of 10 hrs to 10 days, preferably 1-7 days, more preferably 1-5 days, more preferably 1-3 days.

According to the present invention, in the process for producing the molecular sieve, the first oxide source is at least one selected from the group consisting of a silicon source and a germanium source, preferably a silicon source.

According to the present invention, in the process for producing the molecular sieve, the second oxide source is at least one selected from the group consisting of an aluminum source, a boron source, an iron source, a gallium source, a titanium source, a rare earth source, an indium source and a vanadium source, preferably a boron source or a combination of a boron source and at least one selected from the group consisting of an aluminum source, an iron source, a gallium source, a titanium source, a rare earth source, an indium source and a vanadium source, more preferably a boron source or a combination of a boron source and an aluminum source, more preferably a boron source.

According to the present invention, in the process for producing the molecular sieve, as the first oxide source, any corresponding oxide source known in this field for this purpose can be used. For example, if the first oxide is silica, as the first oxide source (silicon source), there may be exemplified silicic acid, silica gel, silica sol, water glass or tetralkoxysilane. If the first oxide is germanium dioxide, as the first oxide source (germanium source), there may be exemplified tetralkoxy germanium, germanium dioxide, germanium nitrate. As the first oxide source, one kind or a mixture of two or more kinds at any ratio therebetween could be used.

According to the present invention, in the process for producing the molecular sieve, as the second oxide source, any corresponding oxide source known in this field for this purpose can be used, including but not limiting to the oxides, alkoxides, oxometallates, acetates, oxalates, ammonium salts, sulfates and nitrates of the corresponding metal in the second oxide. For example, if the second oxide is alumina, as the second oxide source (aluminum source), there may be exemplified aluminum hydroxide, sodium aluminate, aluminum salts, aluminum alkoxides, kaolin or montmorillonite. As aluminum salts, there may be exemplified aluminum sulfate, aluminum nitrate, aluminum carbonate, aluminum phosphate, aluminum chloride or alum. As aluminum alkoxides, there may be exemplified aluminum isopropoxide, aluminum ethoxide, aluminum butoxide. If the second oxide is boron oxide, as the second oxide source (boron source), there may be exemplified boric acid, borate salt, borax, diboron trioxide. If the second oxide is iron oxide, as the second oxide source (iron source), there may be exemplified ferric nitrate, ferric chloride, iron oxide. If the second oxide is gallium oxide, as the second oxide source (gallium source), there may be exemplified gallium nitrate, gallium sulfate, gallium oxide. If the second oxide is titanium oxide, as the second oxide source (titanium source), there may be exemplified titanium tetralkoxide, titania, titanium nitrate. If the second oxide is rare earth oxides, as the second oxide source (rare earth source), there may be exemplified lanthanum oxide, neodymium oxide, yttrium oxide, cerium oxide, lanthanum nitrate, neodymium nitrate, yttrium nitrate, ceric ammonium sulfate. If the second oxide is indium oxide, as the second oxide source (indium source), there may be exemplified indium chloride, indium nitrate, indium oxide. If the second oxide is vanadium oxide, as the second oxide source (vanadium source), there may be exemplified vanadium chloride, ammonium metavanadate, sodium vanadate, vanadium dioxide, vanadyl sulfate. As the second oxide source, one kind or a mixture of two or more kinds at any ratio therebetween could be used.

According to one embodiment of the present invention, for the first oxide source, if multiple oxide sources are used in combination, the ratio by molar between each two oxide sources is generally 1-99.6:99-0.4, preferably 33-99.5:67-0.5, more preferably 50-99:50-1, more preferably 60-99:40-1, more preferably 66-98:34-2, more preferably 66-97:34-3.

According to one embodiment of the present invention, for the second oxide source, if multiple oxide sources are used in combination, the ratio by molar between each two oxide sources is generally 1-99.6:99-0.4, preferably 33-99.5:67-0.5, more preferably 50-99:50-1, more preferably 60-99:40-1, more preferably 66-98:34-2, more preferably 66-97:34-3.

According to one embodiment of the present invention, in the process for producing the molecular sieve, from the point of facilitating obtaining the molecular sieve of the present invention, the mixture does not contain an alkaline source. As the alkaline source, there may be exemplified alkaline substances excepting the first oxide source, the second oxide source and the organic template, specifically there may be exemplified any alkaline source conventionally used in this field for alkalizing the reaction system, more specifically there may be exemplified inorganic alkali containing alkali metal or alkaline earth metal as the cation, especially NaOH and KOH. Herein, by "does not contain an alkaline source", it means not intentionally or on purpose introducing into the mixture an alkaline source.

According to one embodiment of the present invention, in the process for producing the molecular sieve, from the point of facilitating obtaining the molecular sieve of the present invention, the mixture does not contain a fluorine source. As the fluorine source, there may be exemplified fluoride or an aqueous solution thereof, especially HF. Herein, by "does not contain a fluorine source", it means not intentionally or on purpose introducing into the mixture a fluorine source.

According to one embodiment of the present invention, in the process for producing the molecular sieve, from the point of facilitating obtaining the molecular sieve of the present invention, at least at the beginning of the crystallization step, preferably throughout the crystallization step, the mixture is controlled at pH=6-14, preferably pH=7-14, more preferably 8-14, more preferably 8.5-13.5, more preferably 9-12.

According to the present invention, in the process for producing the molecular sieve, the ratio by molar between the first oxide source (as the first oxide), the second oxide source (as the second oxide), the template and water is 1:(0.025-1/3):(0.01-1.0):(4-50), preferably 1:(1/30-1/3):(0.02-0.9):(4-40), more preferably 1:(1/30-1/5):(0.04-0.8):(4-30), with the proviso that the ratio by molar of the first oxide source (as the first oxide) to the second oxide source (as the second oxide) is less than 40, preferably less than 30.

According to this invention, in the process, upon completion of the crystallization step, any separation method conventionally known in this field may be used to isolate a molecular sieve from the obtained reaction mixture as the final product, whereby obtaining the molecular sieve of the present invention. As the separation method, there may be exemplified a method wherein the obtained reaction mixture is filtered, washed and dried. Herein, filtering, washing and drying can be conducted in any manner conventionally known in this field. Specifically, as the filtration, there may be exemplified a method of simply suction filtering the obtained reaction mixture. As the washing, there may be exemplified a method of washing with deionized water. As the drying temperature, there may be exemplified a temperature of 40-250 degrees Celsius, preferably a temperature of 60-150 degrees Celsius, as the drying duration, there may be exemplified a duration of 8-30 h, preferably a duration of 10-20 h. The drying could be conducted under the normal pressure or a reduced pressure.

According to this invention, in the process, if needed, the obtained molecular sieve could be calcinated so as to remove the organic template and any water therefrom, whereby obtaining a calcinated molecular sieve (i.e. the molecular sieve in the calcined form), which corresponds to the molecular sieve of the present invention as well. The calcination could be conducted in any manner conventionally known in this field, for example, the calcination temperature is generally 300-800 degrees Celsius, preferably 400-650 degrees Celsius, while the calcination duration is generally 1-10 h, preferably 3-6 h. Further, the calcination is generally conducted under an oxygen containing atmosphere, for example, under the air atmosphere or under oxygen atmosphere According to the present invention, the obtained molecular sieves may be used in any physical form, for example, powder, particulate or a molded product (for example, strip, clover). These physical forms can be obtained in any manner conventionally known in this field, without any specific limitation thereto.

The molecular sieve according to this invention may be combined with other material, whereby obtaining a molecular sieve composition. As these other materials, there may be exemplified an active material and a non-active material. As the active material, there may be exemplified synthesized zeolites and natural zeolites, as the non-active material (generally referred to as binder), there may be exemplified clay, white earth, silica gel and alumina. As these other materials, one kind or a mixture of two or more kinds at any ratio therebetween could be used. As the amount of these other materials, any amount conventional used in this field could be used, without any specific limitation thereto.

The molecular sieve or the molecular sieve composition of the present invention can be used as an adsorbent, for example, that to be used in a gaseous or liquid phase to isolate at least one component from a mixture made of multiple components. In this way, a part of or substantially all of the at least one component can be isolated from the mixture. Specifically there may be exemplified a way wherein the molecular sieve or the molecular sieve composition is made to contact the mixture, whereby selectively adsorbing this component.

The molecular sieve or the molecular sieve composition of the present invention may be directly or after treated or converted (for example after ion exchanged) in a way conventionally used in this field regarding a molecular sieve used as a catalyst for converting an organic compound (or as a catalytic active component thereof). Specifically, according to the present invention, for example, reactants can be made to conduct a predetermined reaction in the presence of the catalyst for converting an organic compound to obtain the aimed product. As the predetermined reaction, there may be exemplified isomerization of normal paraffins, liquid phase alkylation between benzene and ethylene to produce ethyl benzene, liquid phase alkylation between benzene and propene to produce iso-propyl benzene, butene isomerization, naphtha cracking reaction, alkylation of benzene with ethanol, cyclohexenen hydration, toluene disproportionation to produce p-xylene, alkylation of toluene with methanol to produce p-xylene or disproportionation of iso-propyl naphthalene to produce 2,6-di(iso-propyl) naphthalene. In view of this, as the catalyst for converting an organic compound, there may be exemplified an alkane isomerization catalyst, a catalyst for the alkylation between olefins and aromatics, an olefin isomerization catalyst, a naphtha cracking catalyst, a catalyst for the alkylation between alcohols and aromatics, an olefin hydration catalyst or an aromatic disproportionation catalyst.

EXAMPLE

The following examples illustrate rather than limit this invention.

Example 1

10.995 g of the organic template 4-dimethylamino pyridine, 54.0 g water, 1.879 g boric acid, 22.5 g silica sol (containing $SiO_2$ 40 wt %) were mixed till homogeneous, to obtain a mixture with a ratio (ratio by molar) of:
$SiO_2/B_2O_3$=10
4-dimethylamino pyridine/$SiO_2$=0.6
$H_2O/SiO_2$=25
and then charged into a stainless steel reactor, under stirring at 175 degrees Celsius crystallized for 3 days, upon completion of the crystallization, filtered, washed, dried to obtain a molecular sieve precursor, and then the precursor was at 650 degrees Celsius in air calcined for 6 hours to obtain a molecular sieve.

The XRD data of the resultant molecular sieve were listed in Table 1, and the XRD pattern was as illustrated in FIG. 1.

The resultant molecular sieve has a specific surface area of 297 m²/g, a micropore volume of 0.11 cm³/g.

If determined by inductively coupled plasma-atomic emission spectroscopy (ICP), the sample after calcined has $SiO_2/B_2O_3$=16.2.

TABLE 1

| 2θ/° | d/Å | I/I₀ × 100 |
| --- | --- | --- |
| 6.555 | 13.472 | 36.2 |
| 8.053 | 10.9694 | 85 |
| 9.376 | 9.4243 | 29.9 |
| 11.35 | 7.7899 | 10 |
| 14.145 | 6.2559 | 7.4 |
| 16.278 | 5.4409 | 14.5 |
| 16.831 | 5.2633 | 13.6 |
| 18.624 | 4.7604 | 16.3 |
| 18.956 | 4.6778 | 13.1 |
| 20.221 | 4.3879 | 65 |
| 22.825 | 3.8928 | 81.2 |
| 24.225 | 3.6709 | 100 |
| 26.749 | 3.33 | 20.4 |
| 28.146 | 3.1678 | 20.1 |
| 32.118 | 2.7846 | 3.2 |
| 32.683 | 2.7377 | 3.7 |
| 33.976 | 2.6364 | 2.8 |
| 36.156 | 2.4823 | 24.8 |
| 37.71 | 2.3835 | 3.7 |

Example 2

36.651 g of the organic template 4-dimethylamino pyridine, 45 g water, 3.488 g germanium dioxide, 3.34 g boric acid, 75 g silica sol (containing $SiO_2$ 40 wt %) were mixed till homogeneous, to obtain a mixture with a ratio (ratio by molar) of:
$(SiO_2+GeO_2)/B_2O_3=20$
4-dimethylamino pyridine/$SiO_2=0.6$
$H_2O/SiO_2=10$
and then charged into a stainless steel reactor, under stirring at 180 degrees Celsius crystallized for 2 days, upon completion of the crystallization, filtered, washed, dried, to obtain a molecular sieve in the synthesized form.

The XRD data of the resultant molecular sieve were listed in Table 2 while the XRD pattern is similar to FIG. 1.

The resultant molecular sieve has a specific surface area of 342 m²/g, a micropore volume of 0.12 cm³/g.

If determined by inductively coupled plasma-atomic emission spectroscopy (ICP), the sample after calcined has $SiO_2/B_2O_3=25.2$.

TABLE 2

| 2θ/° | d/Å | $I/I_0 \times 100$ |
|---|---|---|
| 6.517 | 13.5515 | 19.2 |
| 7.993 | 11.0521 | 71.8 |
| 9.336 | 9.465 | 21.7 |
| 11.331 | 7.8028 | 23.7 |
| 14.13 | 6.2626 | 6.7 |
| 16.218 | 5.4609 | 12.2 |
| 16.671 | 5.3134 | 12.4 |
| 18.506 | 4.7904 | 14.4 |
| 18.801 | 4.716 | 10.7 |
| 20.123 | 4.4091 | 60.8 |
| 22.765 | 3.9029 | 71.7 |
| 24.146 | 3.6828 | 100 |
| 26.473 | 3.3641 | 23.4 |
| 27.952 | 3.1894 | 20 |
| 29.25 | 3.0507 | 2.9 |
| 31.955 | 2.7984 | 3.2 |
| 32.668 | 2.7389 | 5.1 |
| 33.057 | 2.7076 | 3.7 |
| 34.678 | 2.5846 | 4 |
| 36.038 | 2.4901 | 26.2 |
| 36.924 | 2.4324 | 4.2 |
| 37.517 | 2.3953 | 4.3 |
| 39.017 | 2.3066 | 3.2 |

Example 3

109.95 g of the organic template 4-dimethylamino pyridine, 540 g water, 9.394 g boric acid, 3.939 g aluminum hydroxide, 225.0 g silica sol (containing $SiO_2$ 40 wt %) were mixed till homogeneous, to obtain a mixture with a ratio (ratio by molar) of:
$SiO_2/(B_2O_3+Al_2O_3)=15$
4-dimethylamino pyridine/$SiO_2=0.6$
$H_2O/SiO_2=25$
and then charged into a stainless steel reactor, under stirring at 170 degrees Celsius crystallized for 3 days, upon completion of the crystallization, filtered, washed, dried, and then the precursor was at 650 degrees Celsius in air calcined for 6 hours to obtain a molecular sieve.

The XRD data of the resultant molecular sieve were listed in Table 3 while the XRD pattern is similar to FIG. 1.

The resultant molecular sieve has a specific surface area of 321 m²/g, a micropore volume of 0.13 cm³/g.

If determined by inductively coupled plasma-atomic emission spectroscopy (ICP), the sample after calcined has $SiO_2/B_2O_3=25.2$, $SiO_2/Al_2O_3=63.0$.

TABLE 3

| 2θ/° | d/Å | $I/I_0 \times 100$ |
|---|---|---|
| 6.612 | 13.3574 | 39.2 |
| 8.034 | 10.9964 | 95.6 |
| 9.395 | 9.4055 | 31.6 |
| 11.329 | 7.8042 | 10.7 |
| 14.145 | 6.2561 | 8.4 |
| 16.201 | 5.4666 | 15.9 |
| 16.73 | 5.2947 | 15.9 |
| 18.882 | 4.696 | 11.7 |
| 20.182 | 4.3964 | 63.4 |
| 22.805 | 3.8963 | 74.4 |
| 24.186 | 3.6768 | 100 |
| 26.453 | 3.3666 | 25.4 |
| 28.011 | 3.1828 | 20.5 |
| 31.936 | 2.8 | 2.9 |
| 32.961 | 2.7152 | 4 |
| 34.496 | 2.5978 | 3.1 |
| 36.058 | 2.4888 | 20.8 |
| 37.729 | 2.3823 | 5.2 |

Example 4

Similar to Example 2, except that $SiO_2/GeO_2=19.2$, $(SiO_2+GeO_2)/B_2O_3=35.2$, 4-dimethylamino pyridine/$SiO_2=0.8$, $H_2O/SiO_2=25$, at 170 degrees Celsius crystallized for 70 hours.

The XRD data of the resultant molecular sieve were listed in Table 4 while the XRD pattern is similar to FIG. 1.

The resultant molecular sieve has a specific surface area of 297 m²/g, a micropore volume of 0.11 cm³/g.

If determined by inductively coupled plasma-atomic emission spectroscopy (ICP), the sample after calcined has $SiO_2/B_2O_3=35.2$.

TABLE 4

| 2θ/° | d/Å | $I/I_0 \times 100$ |
|---|---|---|
| 6.575 | 13.4316 | 21.3 |
| 8.034 | 10.9958 | 79.5 |
| 9.377 | 9.4242 | 25.5 |
| 11.425 | 7.7385 | 28.7 |
| 13.387 | 6.6087 | 3 |
| 14.148 | 6.2549 | 6.8 |
| 16.24 | 5.4536 | 12.8 |
| 16.75 | 5.2885 | 14.8 |
| 18.546 | 4.7802 | 14.2 |
| 18.921 | 4.6864 | 11.4 |
| 20.22 | 4.388 | 63.2 |
| 21.533 | 4.1233 | 2.4 |
| 22.844 | 3.8896 | 74.9 |
| 24.225 | 3.6709 | 100 |
| 26.572 | 3.3518 | 23.9 |
| 28.07 | 3.1762 | 21 |
| 29.271 | 3.0486 | 3.5 |
| 32.012 | 2.7935 | 2.7 |
| 33.02 | 2.7105 | 4.1 |
| 34.516 | 2.5964 | 4.7 |
| 36.136 | 2.4836 | 25.7 |
| 36.95 | 2.4308 | 2.9 |
| 37.637 | 2.3879 | 5 |
| 39.155 | 2.2988 | 3.3 |

Example 5

Similar to Example 1, except that $SiO_2/B_2O_3=27$, 4-dimethylamino pyridine/$SiO_2=0.3$, $H_2O/SiO_2=25$, at 170 degrees Celsius crystallized for 3 days.

The XRD data of the resultant molecular sieve were listed in Table 5 while the XRD pattern is similar to FIG. 1.

The resultant molecular sieve has a specific surface area of 343 m²/g, a micropore volume of 0.13 cm³/g.

If determined by inductively coupled plasma-atomic emission spectroscopy (ICP), the sample after calcined has $SiO_2/B_2O_3$=31.5.

TABLE 5

| 2θ/° | d/Å | I/I₀ × 100 |
|---|---|---|
| 6.575 | 13.4314 | 32.8 |
| 8.053 | 10.9703 | 81.4 |
| 9.452 | 9.3493 | 29.7 |
| 11.309 | 7.818 | 10.8 |
| 14.167 | 6.2465 | 8.8 |
| 16.277 | 5.4412 | 12.4 |
| 16.751 | 5.2882 | 15.4 |
| 18.587 | 4.7698 | 16.4 |
| 18.919 | 4.6869 | 12.7 |
| 20.203 | 4.3917 | 64.1 |
| 22.864 | 3.8863 | 84.4 |
| 24.226 | 3.6708 | 100 |
| 26.711 | 3.3347 | 22.1 |
| 28.072 | 3.176 | 24.5 |
| 29.409 | 3.0346 | 4 |
| 32.08 | 2.7878 | 2.3 |
| 33.018 | 2.7107 | 3.4 |
| 34.541 | 2.5945 | 3.3 |
| 36.154 | 2.4824 | 25.3 |
| 37.072 | 2.423 | 2.3 |
| 37.715 | 2.3831 | 4 |

Example 6

Similar to Example 1, except that $SiO_2/B_2O_3$=20, 4-dimethylamino pyridine/$SiO_2$=0.2, $H_2O$/$SiO_2$=30, at 170 degrees Celsius crystallized for 80 hours.

The XRD data of the resultant molecular sieve were listed in Table 6 while the XRD pattern is similar to FIG. 1.

The resultant molecular sieve has a specific surface area of 347 m²/g, a micropore volume of 0.12 cm³/g.

If determined by inductively coupled plasma-atomic emission spectroscopy (ICP), the sample after calcined has $SiO_2/B_2O_3$=28.0.

TABLE 6

| 2θ/° | d/Å | I/I₀ × 100 |
|---|---|---|
| 6.556 | 13.4705 | 31.5 |
| 8.053 | 10.9705 | 69.9 |
| 9.377 | 9.4239 | 24.2 |
| 11.366 | 7.7789 | 10.3 |
| 14.224 | 6.2214 | 8.2 |
| 16.296 | 5.4349 | 12.9 |
| 16.809 | 5.27 | 14.7 |
| 18.568 | 4.7747 | 15.9 |
| 18.94 | 4.6818 | 13.3 |
| 20.222 | 4.3878 | 63.1 |
| 22.864 | 3.8863 | 83.3 |
| 24.245 | 3.668 | 100 |
| 26.672 | 3.3395 | 24.6 |
| 28.05 | 3.1784 | 21.6 |
| 29.47 | 3.0284 | 3.6 |
| 31.208 | 2.8637 | 1.9 |
| 32.132 | 2.7834 | 3.6 |
| 32.887 | 2.7212 | 3.7 |
| 33.941 | 2.639 | 2.6 |
| 34.674 | 2.5849 | 2.5 |
| 36.155 | 2.4824 | 26.8 |
| 36.855 | 2.4368 | 2.3 |
| 37.677 | 2.3855 | 4.2 |
| 39.184 | 2.2971 | 2.1 |

Example 7

Similar to Example 1, except that $SiO_2/B_2O_3$=10, 4-dimethylamino pyridine/$SiO_2$=0.4, $H_2O$/$SiO_2$=17.5, at 170 degrees Celsius crystallized for 2 days.

The XRD data of the resultant molecular sieve were listed in Table 7 while the XRD pattern is similar to FIG. 1.

The resultant molecular sieve has a specific surface area of 357 m²/g, a micropore volume of 0.13 cm³/g.

If determined by inductively coupled plasma-atomic emission spectroscopy (ICP), the sample after calcined has $SiO_2/B_2O_3$=14.2.

TABLE 7

| 2θ/° | d/Å | I/I₀ × 100 |
|---|---|---|
| 6.595 | 13.3912 | 30.4 |
| 8.054 | 10.9683 | 80.6 |
| 9.416 | 9.3843 | 26.7 |
| 11.347 | 7.7917 | 9.4 |
| 14.169 | 6.2453 | 7.9 |
| 16.3 | 5.4336 | 13.8 |
| 16.79 | 5.2761 | 11.9 |
| 18.605 | 4.7651 | 15.6 |
| 18.923 | 4.6858 | 13.5 |
| 20.223 | 4.3875 | 63.6 |
| 22.865 | 3.8861 | 82.1 |
| 24.264 | 3.6651 | 100 |
| 26.75 | 3.3299 | 22.5 |
| 28.091 | 3.1739 | 20.4 |
| 29.356 | 3.0399 | 3.5 |
| 32.095 | 2.7865 | 4.2 |
| 32.924 | 2.7182 | 3.7 |
| 34.6 | 2.5903 | 2.5 |
| 36.174 | 2.4811 | 26.3 |
| 36.967 | 2.4297 | 2.5 |
| 37.754 | 2.3808 | 4.6 |

Example 8

Similar to Example 1, except that $SiO_2/B_2O_3$=5, 4-dimethylamino pyridine/$SiO_2$=0.5, $H_2O$/$SiO_2$=25, at 170 degrees Celsius crystallized for 66 hours.

The XRD data of the resultant molecular sieve were listed in Table 8 while the XRD pattern is similar to FIG. 1.

The resultant molecular sieve has a specific surface area of 342 m²/g, a micropore volume of 0.12 cm³/g.

If determined by inductively coupled plasma-atomic emission spectroscopy (ICP), the sample after calcined has $SiO_2/B_2O_3$=12.1.

TABLE 8

| 2θ/° | d/Å | I/I₀ × 100 |
|---|---|---|
| 6.594 | 13.3928 | 42.3 |
| 8.053 | 10.9692 | 90.8 |
| 9.415 | 9.386 | 32.5 |
| 11.366 | 7.7787 | 12.1 |
| 14.168 | 6.2461 | 10.4 |
| 16.258 | 5.4473 | 13.3 |
| 16.75 | 5.2884 | 16.8 |
| 18.567 | 4.7748 | 18 |
| 18.901 | 4.6912 | 14.6 |

TABLE 8-continued

| 2θ/° | d/Å | I/I₀ × 100 |
|---|---|---|
| 20.203 | 4.3917 | 67.1 |
| 22.845 | 3.8895 | 83 |
| 24.263 | 3.6652 | 100 |
| 26.691 | 3.3371 | 25.3 |
| 28.032 | 3.1805 | 25.1 |
| 29.256 | 3.0501 | 3.1 |
| 32.919 | 2.7186 | 4.3 |
| 33.933 | 2.6396 | 2.7 |
| 34.494 | 2.598 | 3.2 |
| 36.136 | 2.4836 | 24 |
| 36.914 | 2.433 | 3.5 |
| 37.715 | 2.3832 | 4.7 |

Example 9

Similar to Example 1, except that $SiO_2/B_2O_3=35$, 4-dimethylamino pyridine/$SiO_2=0.36$, $H_2O/SiO_2=25$, at 170 degrees Celsius crystallized for 3 days.

The XRD data of the resultant molecular sieve were listed in Table 9 while the XRD pattern is similar to FIG. 1.

The resultant molecular sieve has a specific surface area of 331 m²/g, a micropore volume of 0.12 cm³/g.

If determined by inductively coupled plasma-atomic emission spectroscopy (ICP), the sample after calcined has $SiO_2/B_2O_3=39.5$.

TABLE 9

| 2θ/° | d/Å | I/I₀ × 100 |
|---|---|---|
| 6.556 | 13.4713 | 41 |
| 8.055 | 10.9668 | 88.3 |
| 9.415 | 9.3855 | 27.7 |
| 11.366 | 7.7787 | 9.7 |
| 14.169 | 6.2457 | 9.4 |
| 16.335 | 5.4221 | 14.9 |
| 16.752 | 5.2879 | 15.4 |
| 18.566 | 4.775 | 16.1 |
| 18.915 | 4.6877 | 11.8 |
| 20.222 | 4.3877 | 62.3 |
| 22.845 | 3.8895 | 78.1 |
| 24.245 | 3.6679 | 100 |
| 26.612 | 3.3468 | 25.5 |
| 28.05 | 3.1784 | 21.5 |
| 29.414 | 3.0341 | 4 |
| 32.092 | 2.7868 | 2.9 |
| 32.847 | 2.7244 | 3.6 |
| 34.49 | 2.5983 | 3.1 |
| 36.155 | 2.4824 | 23.6 |
| 37.657 | 2.3867 | 4.7 |

Example 10

Similar to Example 3, except that aluminum sulfate was used as the aluminum source, $SiO_2/(Al_2O_3+B_2O_3)=20$, 4-dimethylamino pyridine/$SiO_2=0.4$, $H_2O/SiO_2=25$, at 170 degrees Celsius crystallized for 3 days.

The XRD data of the resultant molecular sieve were listed in Table 10 while the XRD pattern is similar to FIG. 1.

The resultant molecular sieve has a specific surface area of 288 m²/g, a micropore volume of 0.09 cm³/g.

If determined by inductively coupled plasma-atomic emission spectroscopy (ICP), the sample after calcined has $SiO_2/B_2O_3=35.2$, $SiO_2/Al_2O_3=63.3$.

TABLE 10

| 2θ/° | d/Å | I/I₀ × 100 |
|---|---|---|
| 6.478 | 13.6332 | 29.6 |
| 7.995 | 11.0488 | 100 |
| 9.375 | 9.4258 | 31.8 |
| 11.268 | 7.8459 | 9 |
| 14.147 | 6.2551 | 8.4 |
| 16.238 | 5.4542 | 13.1 |
| 16.714 | 5.2997 | 14.1 |
| 18.268 | 4.8524 | 20.8 |
| 18.858 | 4.7018 | 12.3 |
| 20.123 | 4.4091 | 64.3 |
| 22.746 | 3.9063 | 76 |
| 24.166 | 3.6798 | 99.9 |
| 26.414 | 3.3714 | 25.4 |
| 27.913 | 3.1937 | 19.7 |
| 31.974 | 2.7968 | 4.3 |
| 32.665 | 2.7392 | 3.5 |
| 34.328 | 2.6101 | 3.3 |
| 36.074 | 2.4877 | 23.5 |
| 37.573 | 2.3918 | 5.1 |

Example 11

Similar to Example 1, except that HF was added as the fluorine source, $SiO_2/B_2O_3=15$, 4-dimethylamino pyridine/$SiO_2=0.5$, $F/SiO_2=0.4$, $H_2O/SiO_2=25$, at 170 degrees Celsius crystallized for 60 hours.

The XRD data of the resultant molecular sieve were listed in Table 11 while the XRD pattern is similar to FIG. 1.

The resultant molecular sieve has a specific surface area of 318 m²/g, a micropore volume of 0.10 cm³/g.

If determined by inductively coupled plasma-atomic emission spectroscopy (ICP), the sample after calcined has $SiO_2/B_2O_3=21.2$.

TABLE 11

| 2θ/° | d/Å | I/I₀ × 100 |
|---|---|---|
| 6.595 | 13.3909 | 30.3 |
| 8.053 | 10.9699 | 100 |
| 9.432 | 9.3693 | 39.2 |
| 11.31 | 7.817 | 12.4 |
| 14.166 | 6.2466 | 8.7 |
| 16.258 | 5.4473 | 12.8 |
| 16.729 | 5.2952 | 14.2 |
| 18.528 | 4.7848 | 15.8 |
| 18.883 | 4.6958 | 12.9 |
| 20.145 | 4.4042 | 31.4 |
| 22.784 | 3.8997 | 48.1 |
| 24.168 | 3.6795 | 55.9 |
| 26.629 | 3.3448 | 20.4 |
| 27.971 | 3.1872 | 20.6 |
| 28.507 | 3.1285 | 4.8 |
| 29.154 | 3.0606 | 4.3 |
| 32.028 | 2.7922 | 1.5 |
| 32.783 | 2.7295 | 3.7 |
| 34.42 | 2.6034 | 3.4 |
| 36.057 | 2.4889 | 10.8 |
| 37.598 | 2.3903 | 4.2 |
| 38.997 | 2.3077 | 1.6 |

Example 12

Similar to Example 1, except that tetra-n-butyl titanate was added as the titanium source, $SiO_2/B_2O_3=10$, $SiO_2/TiO_2=30$, 4-dimethylamino pyridine/$SiO_2=0.8$, $H_2O/SiO_2=25$, at 170 degrees Celsius crystallized for 3 days.

The XRD data of the resultant molecular sieve were listed in Table 12 while the XRD pattern is similar to FIG. 1.

The resultant molecular sieve has a specific surface area of 335 m²/g, a micropore volume of 0.10 cm³/g.

If determined by inductively coupled plasma-atomic emission spectroscopy (ICP), the sample after calcined has $SiO_2/B_2O_3$=16.2, $SiO_2/TiO_2$=39.1.

TABLE 12

| 2θ/° | d/Å | I/I₀ × 100 |
|---|---|---|
| 6.457 | 13.6776 | 34.2 |
| 7.993 | 11.0518 | 95 |
| 9.337 | 9.4641 | 27.1 |
| 11.29 | 7.8307 | 8.2 |
| 14.104 | 6.274 | 7 |
| 16.199 | 5.4672 | 14.5 |
| 16.632 | 5.3259 | 13.6 |
| 18.526 | 4.7853 | 14.9 |
| 20.122 | 4.4093 | 58.9 |
| 22.668 | 3.9195 | 71.9 |
| 24.088 | 3.6915 | 100 |
| 26.396 | 3.3738 | 23.1 |
| 27.991 | 3.185 | 20.4 |
| 31.951 | 2.7987 | 3.1 |
| 32.594 | 2.745 | 4.8 |
| 35.959 | 2.4954 | 24.3 |
| 37.495 | 2.3966 | 5.7 |

Example 13

30 g of the molecular sieve produced in Example 3 in the form of powder was ion-exchanged by an aqueous ammonium nitrate solution (with a concentration of 1 mol/L) for 4 times, filtered, and dried at 110 degrees Celsius, calcined at 500 degrees Celsius in air for 6 hours. Then, 1.5 g of the calcined molecular sieve was charged into a 100 ml stainless steel reactor, further introducing therein 35 g iso-propyl naphthalene, and closed the reactor. At 250° C., under 200 rpm stirring, the reaction was conducted for 48 hours. Upon completion of the reaction, the system was cooled to the room temperature, after centrifugally isolating the molecular sieve powder therefrom, the reaction product was analysed on an Agilent 19091N-236 gas chromatograph, indicating an iso-propyl naphthalene conversion of 26.82%, and a total selectivity to the aimed product 2,6-di(iso-propyl) naphthalene and 2,7-di(iso-propyl) naphthalene of 74.88%.

We claim:

1. An SCM-10 molecular sieve, having an empirical chemical composition of "first oxide second oxide", wherein a ratio by molar of the first oxide to the second oxide is less than 40, the first oxide is at least one compound selected from the group consisting of silica and germanium dioxide, the second oxide is at least one selected from the group consisting of alumina, boron oxide, iron oxide, gallium oxide, titanium oxide, rare earth oxides, indium oxide, and vanadium oxide, and the SCM-10 molecular sieve in a calcined form has an X ray diffraction pattern as substantially illustrated in the following table,

| 2θ (°) [a] | d-spacing (Å) [b] | Relative intensity (I/I₀ × 100) |
|---|---|---|
| 6.50 | 13.59 | w-s |
| 7.98 | 11.07 | s-vs |
| 9.36 | 9.45 | m |
| 11.27 | 7.85 | w-m |
| 20.02 | 4.43 | s |
| 22.65 | 3.92 | vs |
| 24.13 | 3.69 | vs |
| 26.45 | 3.37 | w-m |

-continued

| 2θ (°) [a] | d-spacing (Å) [b] | Relative intensity (I/I₀ × 100) |
|---|---|---|
| 27.92 | 3.19 | w-m |
| 35.95 | 2.50 | m |

[a] ±0.3°,
[b] changed with 2θ.

2. The SCM-10 molecular sieve according to claim 1, wherein the X-ray diffraction pattern further includes X-ray diffraction peaks as substantially illustrated in the following table,

| 2θ (°) [a] | d-spacing (Å) [b] | Relative intensity (I/I₀ × 100) |
|---|---|---|
| 14.12 | 6.27 | w |
| 16.12 | 5.49 | w |
| 18.82 | 4.71 | w |
| 37.52 | 2.40 | w |

[a] ±0.3°,
[b] changed with 2θ.

3. The SCM-10 molecular sieve of claim 1, wherein the ratio by molar of the first oxide to the second oxide is 3 or more and less than 40.

4. The SCM-10 molecular sieve of claim 1, wherein the ratio by molar of the first oxide to the second oxide is in the range of from 5 to 30.

5. An SCM-10 molecular sieve composition, comprising the SCM-10 molecular sieve according to claim 1 and a binder.

6. A method for converting an organic compound, comprising contacting the organic compound with a catalyst comprising the SCM-10 molecular sieve composition according to claim 5.

7. The method according to claim 6, wherein the catalyst is at least one selected from the group consisting of an alkane isomerization catalyst, a catalyst for the alkylation between olefins and aromatics, an olefin isomerization catalyst, a naphtha cracking catalyst, a catalyst for the alkylation between alcohols and aromatics, an olefin hydration catalyst, and an aromatic disproportionation catalyst.

8. The method for separating a component from a mixture, comprising contacting the mixture with an adsorbent comprising the SCM-10 molecular sieve composition according to claim 5.

9. A method for converting an organic compound, comprising contacting the organic compound with a catalyst comprising the SCM-10 molecular sieve according to claim 1.

10. The method according to claim 9, wherein the catalyst is at least one selected from the group consisting of an alkane isomerization catalyst, a catalyst for the alkylation between olefins and aromatics, an olefin isomerization catalyst, a naphtha cracking catalyst, a catalyst for the alkylation between alcohols and aromatics, an olefin hydration catalyst, and an aromatic disproportionation catalyst.

11. The method for separating a component from a mixture, comprising contacting the mixture with an adsorbent comprising the SCM-10 molecular sieve according to claim 1.

12. A process for producing the SCM-10 molecular sieve of claim 1, comprising a step of crystallizing a mixture comprising a first oxide source for the first oxide, a second oxide source for the second oxide, an organic template and water to obtain the molecular sieve, and optionally, a step of calcining the obtained molecular sieve, wherein the organic template is selected from a compound represented by the following formula (A), a quaternary ammonium salt thereof and a quaternary ammonium hydroxide thereof.

13. The process according to claim 12, wherein the mixture does not contain an alkaline source.

14. The process according to claim 12, wherein the mixture does not contain a fluorine source.

15. The process according to claim 12, wherein the mixture has a pH=6-14.

16. The process according to claim 12, wherein the first oxide source is at least one selected from the group consisting of a silicon source and a germanium source, the second oxide source is at least one selected from the group consisting of an aluminum source, a boron source, an iron source, a gallium source, a titanium source, a rare earth source, an indium source and, a vanadium source, the ratio by molar between the first oxide source (calculated as the first oxide), the second oxide source (calculated as the second oxide), the organic template and water is 1:(0.025-1/3):(0.01-1.0):(4-50), with the proviso that the ratio by molar of the first oxide source (calculated as the first oxide) to the second oxide source (calculated as the second oxide) is less than 40.

17. The process of claim 12, wherein the organic template is 4-dimethylamino pyridine,

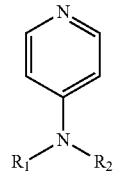

(A)

wherein $R_1$ and $R_2$ is identical to or different from each other, each independently representing a $C_{1-8}$ alkyl.

18. An SCM-10 molecular sieve composition, comprising a SCM-10 molecular sieve produced in line with the process according to claim 12 and a binder.

19. A method for converting an organic compound, comprising contacting the organic compound with a catalyst comprising the SCM-10 molecular sieve produced with the process according to claim 12.

20. The method according to claim 19, wherein the catalyst is at least one selected from the group consisting of an alkane isomerization catalyst, a catalyst for the alkylation between olefins and aromatics, an olefin isomerization catalyst, a naphtha cracking catalyst, a catalyst for the alkylation between alcohols and aromatics, an olefin hydration catalyst, and an aromatic disproportionation catalyst.

21. The method for separating a component from a mixture, comprising contacting the mixture with an adsorbent comprising the SCM-10 molecular sieve produced with the process according to claim 12.

* * * * *

UNITED STATES PATENT AND TRADEMARK OFFICE
CERTIFICATE OF CORRECTION

| | |
|---|---|
| PATENT NO. | : 10,399,068 B2 |
| APPLICATION NO. | : 15/347094 |
| DATED | : September 3, 2019 |
| INVENTOR(S) | : Weimin Yang et al. |

Page 1 of 1

It is certified that error appears in the above-identified patent and that said Letters Patent is hereby corrected as shown below:

On the Title Page

Item (73) Line 3 to Line 5, the second assignee's name and location reading:
-RESEARCH INSTITUTE OF PETROCHEMICAL TECHNOLOGY, SINOPEC, Beijing (CN)-

Should be changed to:
-SHANGHAI RESEARCH INSTITUTE OF PETROCHEMICAL TECHNOLOGY, SINOPEC, Shanghai (CN)-

Signed and Sealed this
Seventh Day of January, 2020

Andrei Iancu
*Director of the United States Patent and Trademark Office*